United States Patent [19]
Schultz

[11] Patent Number: 6,063,385
[45] Date of Patent: May 16, 2000

[54] DNA VACCINE FOR PARVOVIRUS

[75] Inventor: Ronald D. Schultz, Verona, Wis.

[73] Assignee: Wisconsin Alumni Research Foundation, Madison, Wis.

[21] Appl. No.: 08/966,114

[22] Filed: Nov. 7, 1997

[51] Int. Cl.[7] .................................................. A61K 39/12
[52] U.S. Cl. .................................... 424/233.1; 424/199.1; 935/56
[58] Field of Search .............................. 424/199.1, 93.2, 424/233.1; 536/23.1; 935/12, 27, 56

[56] References Cited

U.S. PATENT DOCUMENTS

| | | | |
|---|---|---|---|
| 4,971,793 | 11/1990 | Wood et al. | 424/88 |
| 5,316,764 | 5/1994 | Walsh | 424/89 |

OTHER PUBLICATIONS

Shen et al The Conference of Research Workers in Animal Diseases, Abstracts, Presented at the 77th Annual Meeting, Nov. 11, 12, 1996, p. 60.

Jiang et al IVVDC First International Veterinary Vaccines and Diagnostics Conf., Jul. 27–31, 1997.

Bruce Smith IBC's Internal. Symp. Vet. Vaccines, Apr. 15, 1997.

Appel et al The Veterinary Record pp. 156–159, 1979.

Rimmelzwaan et al J. Gen. Virol. 71: 2321–2329, 1990.

K.I. Berns, "Parvoviridae: The Viruses and Their Replication", *Fields Virology*, 3rd Ed., B.N. Fields, et al., Lippincott–Raven Publishers, Philadelphia, 2:2173–2192, 1996.

M.J.G. Appel, et al., "Isolation and Immunization Studies of a Canine Parvo–like Virus from Dogs with Haemmorrhagic Enteritis", *The Veterinary Record*, pp. 156–159, 1979.

P.R. Paradiso, et al., "Canine Parvovirus: a Biochemical and Ultrstructural Characterization", *J. Gen. Virol.*, 62:113–125, 1982.

A.P. Reed, et al., "Nucleotide Sequence and Genome Organization of Canine Parvovirus", *J. Virol.*, 62:266–276, 1988.

S.L. Rhode, III, "Nucleotide Sequence of the Coat Protein Gene of Canine Parvovirus", *J. Virol.*, 54:630–633, 1985.

G.F. Rimmelzwaan, et al., "Delineaton of Canine parvovirus T cell Epitopes with Peripheral Blood Mononuclear Cells and T cell Clones from Immunized Dogs", *J. Gen. Virol.*, 71:2321–2329, 1990.

C.R. Parrish, et al., "Canine Host Range and a Specific Epitope Map along with Variant Sequences in the Capsid Protein Gene of Canine Parvovirus and Related Feline, Mink, and Raccoon Parvoviruses", *Virology*, 166:293–307, 1988.

C.R. Parrish, "Mapping Specific Functions in the Capsid Structure of Canine Parvovirus and Feline Panleukopenia Virus Using Infectious Plasmid Clones", *Virology* 183:195–205, 1991.

B.F. Smith, et al., "Immunization of Dogs with a Plasmid Encoding the Nucleocapsid Gene(s) of Canine Parvovirus Confers Protective Immunity to Virus Challenge", IBC's International Symposium, Philadelphia, Pennsylvania, Apr. 14–15, 1997.

W. Jiang, et al., "Nucleic Acid Immunization Protests Dogs Against Challenge with Virulent Canine Parvovirus", First International Veterinary Vaccines and Diagnostics Conference, Madison, Wisconsin, Jul. 27–31, 1997.

C.K. Shen, et al., "DNA Vaccines for Canine Parvovirus Type 2 (CPV–2): What They Can and Can't Do", The Conference of Research Workers in Animal Disease, Iowa State University Press/Ames, Nov. 11–12, 1996.

C.K. Shen, et al., "DNA Vaccines for Canine Parvovirus Type 2 (CPV–2): What They can and Can't Do", First International Veterinary Vaccines and Diagnostics Conference, Madison, Wisconsin, Jul. 27–31, 1997.

*Primary Examiner*—Donna C. Wortman
*Assistant Examiner*—Brenda G. Brumback
*Attorney, Agent, or Firm*—Quarles & Brady LLP

[57] ABSTRACT

Disclosed herein are methods for vaccinating mammals against parvovirus. In one form, a recombinant, replication incompetent vector containing DNA coding for canine parvoviral capsid protein is administered to a dog while the pup's maternal antibodies are still functioning. This acts to prime T-helper cells. A second administration of either canine parvoviral capsid protein, or a construct capable of expressing it, is then administered. The latter administration immunizes the mammal notwithstanding the maternal antibody effect.

4 Claims, 3 Drawing Sheets

DNA VACCINE FOR PARVOVIRUS

CROSS REFERENCES TO RELATED APPLICATIONS

Not applicable.

STATEMENT REGARDING FEDERALLY SPONSORED RESEARCH

Not applicable.

BACKGROUND OF THE INVENTION

The present invention relates to DNA constructs useful to assist in immunization against parvovirus. More particularly, it relates to methods of using such constructs to minimize interference by maternal antibodies.

Various types of disease causing parvovirus are known. See generally B. N. Fields et al., Fields Virology, 3rd Edition, Chapter 69 (1996) (structure of mammalian parvovirus virion). For example, in the 1970's a new viral disease of dogs causing fatal enteritis and/or myocarditis was observed. The virus was named canine parvovirus-2 (CPV-2) in order to distinguish it from an unrelated non-pathogenic canine parvovirus (CPV-1) which had been isolated earlier. See generally 105 Vet. Rec. 156–159 (1979); P. R. Paradiso et al., 62 J. Gen. Virol. 113–125 (1982) (structural characterization of canine parvovirus); A. P. Reed et al., 62 J. Virol. 266–276 (1988) (nucleotide sequence of canine parvovirus-2); S. L. Rhode, 54 J. Virol. 630–633 (1985) (nucleotide sequence of coat protein gene of canine parvovirus-2). The disclosure of these publications, and of all other publications referred to herein are incorporated by reference as if fully set forth herein.

Due to the unusually high morbidity and mortality caused by this virus, substantial efforts have been made to develop vaccines. Vaccines containing feline parvovirus or mink enteritis virus were initially tried. These heterotypic vaccines provided some (albeit insufficient) protective immunity from CPV-2 disease.

Other workers tried to attenuate CPV-2 as well as to make killed CPV-2 vaccines. CPV-2 vaccines, especially the modified live vaccines, provided better protective immunity than the feline and mink vaccines. However, they failed to effectively override maternal antibody, leaving young puppies at risk to infection for weeks or months. This risk period, referred to as the "window of vulnerability", varied among vaccines, but was shown to be as great as 15 weeks in some cases.

Methods were tried to further improve the CPV-2 vaccines, so that the "window of vulnerability" could be shortened. These included 1) liposome encapsulated virus, 2) macrophage engulfed virus, 3) slow release of virus systematically or in the intestinal tract, 4) the use of new heterotypic parvovirus vaccines, 5) vaccinia virus vectored CPV-2 vaccines, 6) vaccines with significantly increased amount of killed or live virus, 7) vaccines with strains of virus that were more immunogenic (e.g. lower number of tissue culture passages, new isolates of CPV-2), and 8) virus-antibody complexes. Most effective was increasing the titer of vaccine virus or increasing the immunogenicity of vaccine virus, which reduced, but did not eliminate the window of vulnerability.

In unrelated work, DNA vaccines for certain viruses other than parvovirus have been developed. In one approach, purified "naked" DNA appears to be taken up and expressed by cells in vivo. A related approach has been the use of a recombinant vector (e.g. a plasmid or a virus such as adenovirus, retrovirus, avipox, herpes or vaccinia virus).

Thus, it can be seen that a need exists for an improved canine parvovirus vaccine.

BRIEF SUMMARY OF THE INVENTION

In one aspect the invention provides a method for immunizing a mammal (preferably a canine animal such as a dog) to a parvovirus. One administers to the mammal a recombinant, replication incompetent vector having a nucleic acid sequence coding for at least an epitope of a parvovirus capsid protein (preferably an epitope of viral capsid protein 1 and/or 2 of canine parvovirus-2). The administration of the vector takes place within twelve weeks after the birth of the mammal. Still within twelve weeks after the birth of the mammal, but after the administration of the vector, one administers to the mammal a composition which contains either parvovirus capsid protein, or a nucleic acid sequence coding for expression of parvovirus capsid protein. This causes the mammal to be immunized against the parvovirus until at least twelve weeks after birth of the mammal.

The vector is preferably a DNA plasmid. The administration is preferably by intramuscular injection. Alternatively, it may be by intravenous injection, intranasal exposure, oral administration, and/or by other means.

The preferred dosages of the vector are in the range of 25 $\mu$g. to 200 $\mu$g. The second administration can, if desired, be another similar administration of the vector. Alternatively, it can be an administration of one of the various other prior art vaccines (used as they have been previously been used) which contain the specified protein(s) or are capable of expressing it (them).

In dogs, the vector is preferably injected between the second and seventh week after birth, (preferably by the sixth week). At this point, the maternal antibody protection is beginning to decrease, yet is still capable of interfering with the effectiveness of prior art vaccines.

More than eight hours (preferably between two and four weeks) after the initial vector administration, the second administration occurs. Even though the maternal antibodies may still then be very active, the first administration acts as an immune primer. The priming appears to be due to T-helper cell proliferation. Once this has occurred, the second administration is permitted to become effective notwithstanding the presence of the residual maternal antibody protection. For purposes of this patent, "immunized" shall mean absence of visually observable disease caused by the virus after challenge with a single does of $1 \times 10^6$ TCID$_{50}$ of the virus via oral-nasal inoculation (the natural route of infection).

The objects of the present invention include providing methods of the above kind:

(a) that provide immunity against a parvovirus such as canine parvovirus-2;

(b) which reduce or eliminate the window of vulnerability that is caused by maternal antibodies interfering with vaccinations; and (c) which can safely be used in young mammals such as puppies.

These and still other objects and advantages of the present invention will be apparent from the description which follows. The following description is merely of the preferred embodiments. Thus, the claims should be looked to in order to understand the full scope of the invention.

DETAILED DESCRIPTION

General Overview

Figure 1:
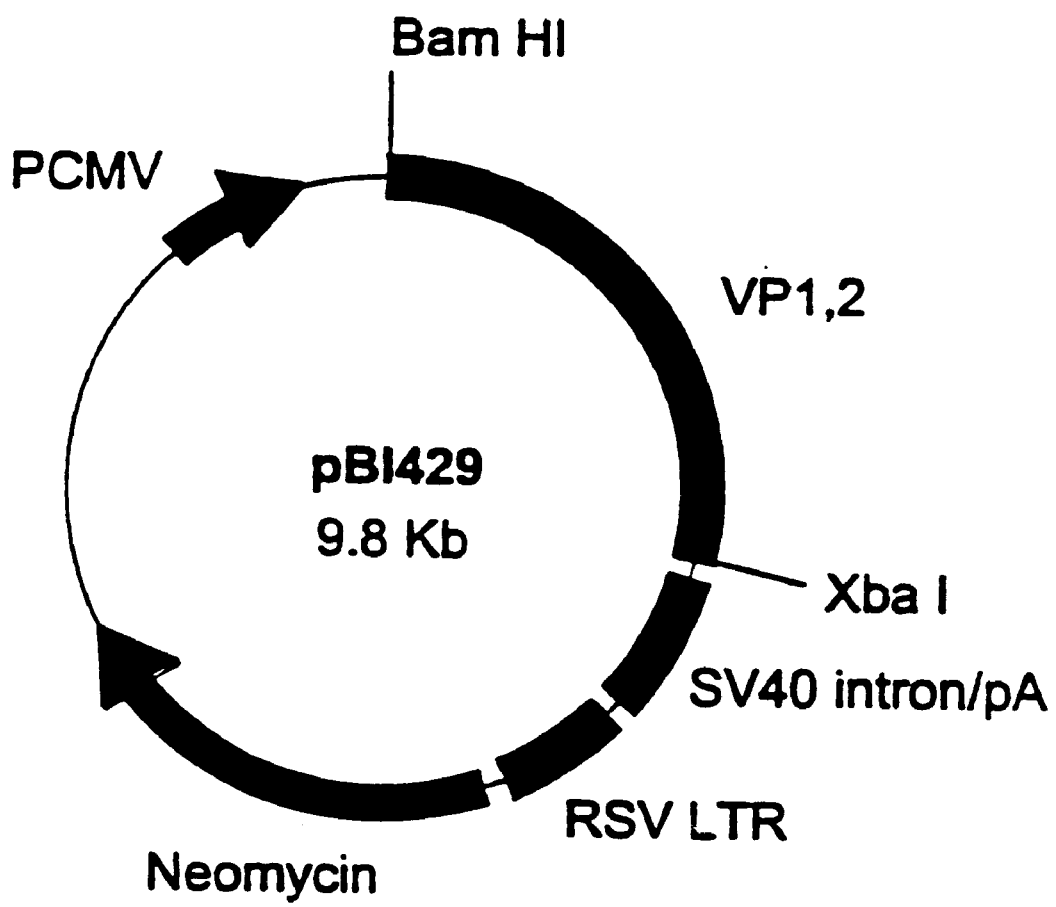
FIG. 1 depicts plasmid pBI429, which contains both the VP1 and VP2 DNA.
Figure 2:
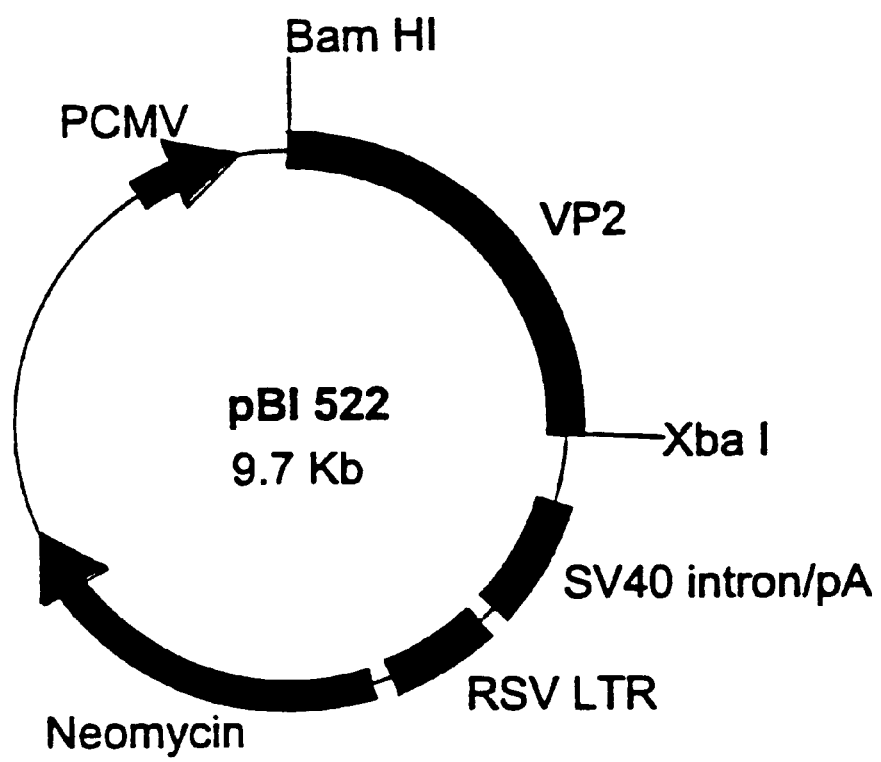
FIG. 2 depicts plasmid pBI522, which contains the VP2 DNA.
Figure 3:
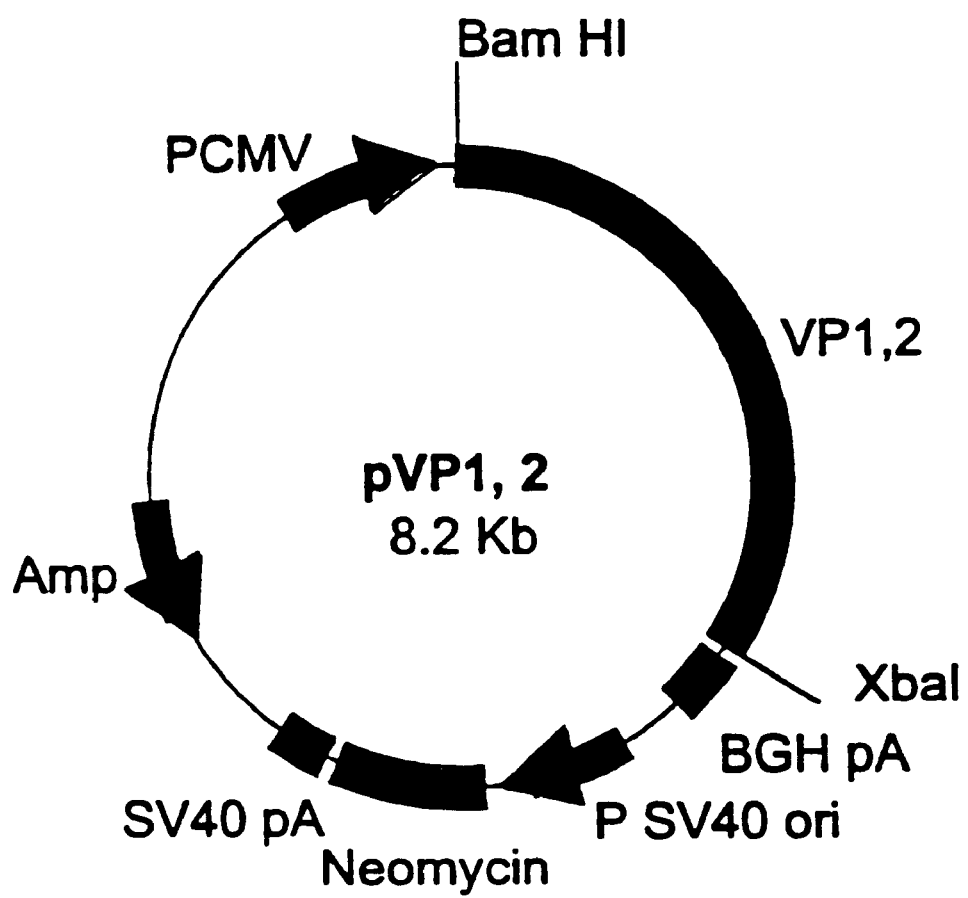
FIG. 3 depicts plasmid pVP1,2 which contains both the VP1 and VP2 DNA.

We use nucleic acid (e.g. DNA) parvoviral capsid protein vaccines to eliminate the window of vulnerability, something not previously achieved with the modified live virus (MLV) or non-infectious (killed) conventional, or the other prior art CPV-2 vaccines. We used 30 five week old beagle puppies, all with passively acquired maternal antibodies to CPV-2. Neither MLV or killed CPV-2 could immunize these pups if immunizations were tried five or six weeks after birth, (due to interference from the passive acquired antibody).

Three groups of pups received one of three different DNA vaccines and the fourth group received saline (control group). The number of pups in any one group varied between 12 for VP1,2 DNA vaccine to 4 pups in the control group. One half the pups in the vaccine groups received 200 $\mu$g of DNA and the other half received 100 $\mu$g of the DNA vaccine.

After the vaccination with the three different DNA vaccines some pups were given saline, others received a second DNA vaccination, and others were inoculated with conventional MLV or killed vaccines. One day to six days after the second vaccination all 30 pups were challenged with virulent virus. The results of this study showed that:

1. Those pups not vaccinated (saline control group) all became sick after challenge and all died.
2. Those pups that were given the DNA vaccine at 6 weeks and not revaccinated prior to challenge received partial protection. 30% were protected (since they did not get sick), and 70% got sick and died. This showed that the one dose of the vector DNA, given at a time when passive antibody was prevalent, provided some protection, but did not provide an acceptable level of immunity.
3. Those pups that were given DNA vaccine and then vaccinated again with DNA vaccine, MLV or killed vaccine (as little as one day prior to challenge) did not get sick and there was no mortality. This should be contrasted with the results for pups receiving only one dose of DNA, MLV or killed vaccine (as little as one day prior to challenge) where all pups would get sick and die.

This study confirms a novel method to overcome the interference of vaccinal immunity caused by passively acquired maternal antibody, thus eliminating the window of vulnerability. The process has the advantage of being able to use a safe, non-infectious, non-allergenic product (DNA vaccine) at a very young age when maternal antibody would otherwise have prevented immunization with modified live or killed vaccines. We follow then at a later time with one of a variety of accepted different vaccines.

Thus, a veterinarian does not have to risk changing to a different vaccine when practicing the present invention. He or she merely adds another injection to the normal protocol.

This first dose of vector, the "pre-immunization primer dose", is able to provide essentially immediate protective immunity after a second dose of vaccine. In this regard, the "primed immune response", when subsequently stimulated with a second dose of DNA vaccine or a MLV vaccine or a killed vaccine can respond with the very rapid development of a protective immune response. This protection can be seen within a period of time as short as one day or possibly less.

This effect seems to be accomplished by the expansion of a population of T helper ($T_H$) cells that can later assist antigen reactive B cells to produce CPV-2 antibody in a very short period of time, thus providing a protective cellular and humoral "immune response".

Structure Of Canine Parvovirus

CPV-2 is a member of the family-Paravoviridae and it belongs to Parvovirus sub-genus A, the group of autonomous parvovirus that is distinguished by their ability to replicate in actively dividing cells without co-infection with an unrelated helper virus. The capsid of CPV-2 particles is typical of the parvoviruses and is constructed of three structural proteins of molecular weight 82,300 (VP1), 67,300 (VP2) and 63,500 (VP3). VP3 is formed from VP2 by proteolytic cleavage, and this normally occurs after assembly of the virions. VP2 is the major capsid protein with the whole sequence of VP3 contained within VP2, and the primary structure of VP2 corresponds to that of the 584 carboxylterminal residues of VP1.

Various epitopes of canine parvoviral capsid protein have previously been described in F. Rimmelzwaan et al., 71 J. Gen. Virol. 2321–2329 (1990) and elsewhere.

Materials And Methods

EXAMPLE

Plasmids pBI429 and pBI522 (see FIGS. 1 and 2) were kindly provided by Colin R. Parrish (James A. Baker Institute for Animal Health, Cornell University). These are two different prior art clones that contain the capsid protein gene(s) of canine parvovirus-2. Alternatively, we took these sequences and inserted them into a mammalian cell expression vector such as PCDNA I/neo (Invitrogen) or related Invitrogen vectors so that the genes could be expressed under the control of cytomegalovirus (CMV) immediate early promoter.

The pBI429 (FIG. 1) contains the entire VP1 and VP2 gene (from XmnI~ right hand end). pBI522 (FIG. 2) contains a spliced version of the gene, so it expresses only VP2.

The new recombinant, pVP1,2 (FIG. 3), was constructed by having pBI429 digested with Bam HI and Xba I. The fragment containing the entire VP1 and VP2 sequence was isolated by electrophoresis on a 1% agarose gel, electroeluted, extracted with phenol/chloroform and chloroform, ethanol precipitated, and ligated into pCDNA 3 (Invitrogen) which was previously digested with Bam HI and Xba I.

For reporter gene expression, the recombinant plasmid DNA contained *Escherichia coli* β-galactosidase gene (Lac Z) driven by the immediate-early promotor of cytomegalovirus. (CMV) (Waisman Center, UW-Madison). The JM109 strain of *Escherichia coli* was transformed and grown under ampicillin selection. Plasmid DNAs were purified with a QIAGEN plasmid kit (Chatsworth, Calif.). The purification protocols are based on a modified alkaline lysis procedure followed by binding of plasmid DNA to QIAGEN anion exchange resin under appropriate low salt and pH conditions.

Following isopropanol precipitation, the pellet was washed twice with 70% ethanol, air dried and redissolved in sterile water at a final concentration of 1 mg/ml. It was then aliquoted and stored at −20° C. until required for intramuscular injection.

Plasmid was administered to the dogs at doses of 100 $\mu$g or 200 $\mu$g. Blood samples were collected weekly for analysis. Prior to injection the plasmid was dissolved in sterile 0.9% saline. Each pup was injected intramuscularly with 1 ml of DNA solution.

DNA vaccinations with or without cationic liposomes appeared to stimulate an immune response. To test the protective immunity provided by DNA vaccines (with or without additional vaccination), puppies were challenged with virulent CPV-2 virus at a dose of $1 \times 10^6$ TCID$_{50}$. All of the puppies who received the priming following by the second administration were protected from death.

It will be apparent that the foregoing illustrates certain preferred embodiments of the invention, but are not limitative of scope. For example, instead of intramuscular injection, the first administration could be by any of the wide variety of known prior techniques for vaccinating against canine parvoviral virus (e.g. intravenous; intranasal; oral). Further, while in the preferred embodiment dogs are innoculated with dog capsid protein expressing DNA, the expressing DNA could be from other parvoviral sources. Moreover, the mammal to be treated could be another type of mammal (e.g. cat).

Accordingly, such alternatives and other modifications are to be considered as forming a part of the invention insofar as they fall within the spirit and scope of the appended claims.

Industrial Applicability

The invention thus provides a method for reducing the incidence of parvoviral infection in young animals.

I claim:

1. A method for immunizing a dog to a canine parvovirus, comprising the steps of:

administering to the dog a recombinant, replication incompetent vector having a nucleic acid sequence coding for an immunogenic parvovirus capsid protein selected from the group consisting of (a) a protein comprising the entire canine parvovirus protein VP1 and (b) a protein comprising the entire canine parvovirus protein VP2, wherein the administration takes place within twelve weeks after the birth of the dog; and thereafter, and still within twelve weeks after the birth of the dog, administering to the dog a composition selected from the group consisting of (c) a protein comprising the entire canine parvovirus protein VP1, (d) a protein comprising the entire canine parvovirus protein VP2, (e) a nucleic acid sequence coding for a protein comprising the entire canine parvovirus protein VP1, and (f) a nucleic acid sequence coding for a protein comprising the entire canine parvovirus protein VP2;

whereby the dog is immunized against the parvovirus until at least twelve weeks after the birth of the dog.

2. The method of claim 1, wherein the canine parvovirus which the dog is immunized against is canine parvovirus-2.

3. The method of claim 1, wherein the vector is a plasmid.

4. The method of claim 1, wherein at least the first of said administrations is via intramuscular injection.

* * * * *